United States Patent
Nacharaju et al.

(10) Patent No.: US 8,258,362 B2
(45) Date of Patent: Sep. 4, 2012

(54) METHOD FOR THE PRODUCTION OF α, ω-OLEFINS BY USING THE COPPER CATALYZED COUPLING REACTION OF A GRIGNARD REAGENT WITH AN ALLYLIC SUBSTRATE

(75) Inventors: Krishnamurthy Nacharaju, Hilliard, OH (US); Paul D. Taylor, Dublin, OH (US); Mark J. Cooney, Circleville, OH (US); Larry A. Crabtree, Chillicothe, OH (US)

(73) Assignee: ISP Investments Inc., Wilmington, DE (US)

( * ) Notice: Subject to any disclaimer, the term of this patent is extended or adjusted under 35 U.S.C. 154(b) by 240 days.

(21) Appl. No.: 12/773,458

(22) Filed: May 4, 2010

(65) Prior Publication Data

US 2010/0280299 A1    Nov. 4, 2010

Related U.S. Application Data

(60) Provisional application No. 61/175,223, filed on May 4, 2009.

(51) Int. Cl.
*C07C 2/76* (2006.01)

(52) U.S. Cl. ......... 585/601; 585/603; 585/604; 585/621

(58) Field of Classification Search ................ None
See application file for complete search history.

(56) References Cited

U.S. PATENT DOCUMENTS

| | | | | |
|---|---|---|---|---|
| 3,948,803 | A | * | 4/1976 | Carney .......................... 502/169 |
| 4,292,454 | A | * | 9/1981 | Cardenas et al. ............... 585/16 |
| 5,073,659 | A | * | 12/1991 | Hamamura et al. .......... 585/600 |
| 5,133,903 | A | * | 7/1992 | Gull et al. ...................... 554/130 |
| 5,296,133 | A | * | 3/1994 | Kramer et al. ................. 208/400 |
| 5,298,157 | A | * | 3/1994 | Kramer et al. ................. 208/400 |
| 2005/0113624 | A1 | * | 5/2005 | Smith et al. .................... 585/730 |
| 2008/0194400 | A1 | * | 8/2008 | Schmidt ......................... 502/223 |

* cited by examiner

*Primary Examiner* — Tam M Nguyen

(74) *Attorney, Agent, or Firm* — Wiliam J. Davis; Thompson Hine LLP

(57) ABSTRACT

A process for the synthesis of linear α,ω-diolefins from an allylic substrate comprises the steps of a) forming the bis-Grignard reagent $XMgCH_2(CH_2)_nCH_2MgX$ from an α,ω-acyclic dihalide with X being a halogen; b) preparing a solution comprising an allylic substrate and a copper catalyst; c) catalyzing a coupling reaction by adding to the solution of step (b) the bis-Grignard reagent of step (a); and d) isolating and purifying the α,ω-olefin coupling reaction product.

14 Claims, No Drawings

METHOD FOR THE PRODUCTION OF α, ω-OLEFINS BY USING THE COPPER CATALYZED COUPLING REACTION OF A GRIGNARD REAGENT WITH AN ALLYLIC SUBSTRATE

CROSS REFERENCE TO RELATED APPLICATION

This application claims the benefit of U.S. Provisional Patent Application Ser. No. 61/175,223 filed on May 4, 2009, the entire contents of which are hereby incorporated by reference.

BACKGROUND

This present application relates to the process of synthesizing α,ω-Olefins from an allylic substrate by utilizing a copper catalyzed coupling reaction with a Grignard reagent. More still particularly, the present application relates to the process of synthesizing α,ω-diolefins and more particularly, to a process for obtaining symmetrical α,ω-dienes. The process involves formation of the Grignard reagents from acyclic α,ω-dihalides that would typically contain from 3 to 10 carbons which in turn react with an allylic halide or ester in the presence of a copper catalyst. The process provides improved yields, and a simpler, more routine method of obtaining α,ω-Olefins. The present application further illustrates the use of symmetrical dienes in the various commercial synthetic routes.

Conventionally, α,ω-olefins have been prepared using a variety of methods including but not limited to the following: olefin metathesis (as disclosed in U.S. Pat. No. 5,342,985); acetate pyrolysis (*Neftekhimiya* 1969, 9, 767-770); and the pyrolysis of cycloalkenes in the presence of water and an amine or ammonia regulator at elevated temperatures (U.S. Pat. No. 3,622,646).

Amongst the available methods, olefin metathesis is the most common methodology and is an extremely versatile reaction for diene formation that is found in the literature. However, olefin metatheses reactions often result in complex reaction mixtures (as reported in *The Journal of Molecular Catalysis A: Chemical* 1998, 133, 17-27) and sometimes require higher temperatures and pressures as is the case in U.S. Pat. No. 3,424,811.

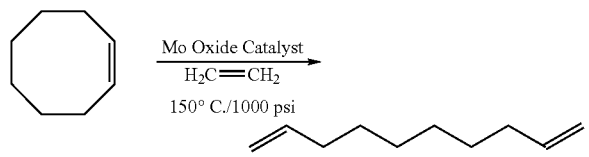

Symmetrical dienes are reported in U.S. Pat. No. 3,878,262 with a yield value in the 80 to 90% range for 1,9-decadiene; however, the reaction was carried out at about 340° C. and 600 psi.

Recent advances in catalyst technology have not only improved yields but have reduced the reaction temperature to 30° C. and the pressure to 8 bar (116 psi) as disclosed in U.S. Pat. No. 5,342,985 which reported a 91% yield of 1,9-decadiene.

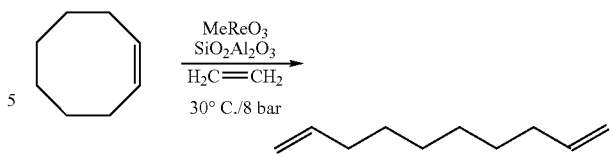

Many facilities do not have the capability of carrying out reactions under extreme conditions (even with the appropriate choice among the wide range of available catalysts, the support required heating at 550° C. for 2 hours prior to carrying out the metathesis reaction) or do not have the continuous feed equipment that is usually required for olefin metathesis to be successful. Facilities without the more specialized equipment would use a more traditional approach which includes, but is not necessarily limited to, dehydrohalogenation and Grignard chemistry.

Dehydrohalogenation is a time tested technique for the formation of an alkene. The technique generally works well in the laboratory and in production; however, there are potential problems associated with that type of chemistry including the possibility of passing over potentially offensive odors into a distilled product. The starting materials, which are in this case long chain α,ω-diols can be costly and the depicted process requires scrubbing to remove sulfur dioxide and hydrogen chloride. The actual elimination step requires the capability of being able to safely handle a strong moisture sensitive base like potassium t-butoxide in bulk.

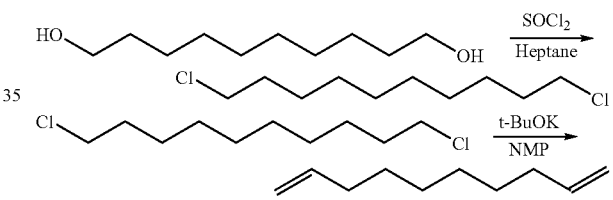

The use of Grignard chemistry eliminates potential odor problems that may be associated with the above dehydrohalogenation chemistry and usually yields a product mixture with fewer impurities. In general, the raw materials are less costly and emissions are more easily dealt with. The chemistry is very well known and has been used for a few years more than one century (for a short review see *Science of Synthesis* 2004, 7, 573-596).

Grignard reagents are extremely valuable in chemical synthesis for the formation of carbon-carbon, carbon-phosphorus, carbon-silicon and other carbon-heteroatom bonds. Bonds of these types are formed with coupling reactions which fall into the class of a nucleophilic substitution reaction. A wide variety of substrates including carbon disulfide, carbon dioxide, aldehydes, ketones, esters, carboxylic acids (in particular formic acid where one equivalent of Grignard reagent is used to form the salt of the acid), acid halides, nitriles, epoxides, and a variety of phosphorous and silicon reagents have been used in such reactions with the only limitation being that the substrate cannot have an acidic hydrogen. The coupling reaction of an alkyl halide with a Grignard reagent has been known for more than 50 years and has some synthetic utility (see Kharasch and Reinmuth *Grignard Reactions of Nonmetallic Substances*; Prentice Hall: Englewood Cliffs, N.J., 1954 pp. 1046-1165). More recently Grignard reagents have been used by Knochel for the formation of polyfunctional aryl and heteroaryl magnesium reagents via a bromine magnesium exchange (see Abarbri, M.; Dehmel, F.; Knochel, P. *Tetrahedron Lett.* 1999, 40, 7449-7453).

The copper catalyzed coupling reaction of a Grignard reagent with an organic halide, which is commonly referred to as a halide displacement reaction, was first reported in 1971 by Kochi and Tamura (*J. Am. Chem. Soc.* 1971, 93, 1487, *Synthesis* 1971, 303, *J. Organomet. Chem.* 1972, 42, 205). In the Synthesis paper the authors reported the coupling reaction of n-butylmagnesium bromide with n-hexyl bromide in the presence of dilithiumtetrachlorocuprate ($Li_2CuCl_4$). Since that report the use of $Li_2CuCl_4$ in coupling reactions has been quite extensive and is prominent in the synthesis of pheromones as well as in the synthesis of α,ω-olefins. One of the more interesting uses of this copper catalyzed coupling reaction may be found in U.S. Pat. No. 4,912,253 where sorbyl acetate was coupled with the Grignard prepared from the magnesium salt of chlorohexanol to form the codling moth (*Laspeyresia pomonella*) sex pheromone 8,10-dodecadien-1-ol on a metric ton scale. α,ω-olefins have been formed by coupling 4-pentenylmagnesium bromide with the bis-tosylate of 1,5-pentanediol to form 1,14-pentadecadiene in 81% yield (*Tetrahedron* 1991, 47, 6287-6292). 1,9-Decadiene has been prepared by the $Li_2CuCl_4$ catalyzed coupling reaction of 1,4-dibromobutane with allylmagnesium bromide at 25° C. in 38% yield (*Synthetic Communications* 1994, 24, 459-463).

U.S. Pat. No. 4,228,313 discloses a process for the coupling of a Grignard reagent with an allylic halide (typically a chloride) in an aprotic solvent (THF or ether) in the presence of a catalyst ($CuCl$, $CuCl_2$, $Li_2CuCl_4$, $FeCl_3$, and a variety of nickel and cobalt catalysts) for the purpose of improving the yield and increasing selectivity for the synthesis of a $C_{15}$ compounds that make up a group of compounds related to vitamin E. In this invention the Grignard reagent was stirred with the catalyst at 35° C. for 1 hour followed by addition of this solution to the allylic chloride at the desired reaction temperature (typically 35° C.) or by adding the catalyst to the allylic halide and then carrying out the coupling reaction by the addition of the Grignard reagent to that solution at the desired reaction temperature. It should be noted that while there are some similarities of the invention outlined in U.S. Pat. No. 4,228,313 to the current invention there are differences with the primary one being the use of a bis-Grignard reagent for the exclusive formation of an α,ω-olefin. This example simply indicates how useful the copper catalyzed coupling reaction pioneered by Kochi and Tamura has been for chemistry in general.

The formation of a bis-Grignard reagent from an α,ω-dihalide is known in the literature; however, the use of such reagents does not appear to be wide spread. The Grignard reagent formed from 1,4-dibromobutane was first used in a coupling reaction with 2 equivalents of allyl bromide in 1911 as reported by Reformatskii et al (*Berichte der Deutschen Chemischen Gesellschaft* 1911, 44, 1885-1886) and then again by Braun, Deutsch, and Schnatloch in 1912 (*Berichte der Deutschen Chemischen Gesellschaft* 1912, 45, 1246-1263, 1,4-diiodobutane was used to prepare the bis-Grignard reagent). The preparation and use of 1,4-bis(chloromagnesium)butane was reported in U.S. Patent Application Publication No. 2003/0004357 and a similar example may be found in DE 4,411,101 (neither patent uses the bis-Grignard reagent in a halide displacement reaction). A more recent example of the coupling of a bis-Grignard reagent, for example, 1,5-bis(bromomagnesium)pentane, with a halide or organic ester such as an acetate (OAc) or an inorganic ester such as a p-toluenesulfonate (tosylate or OTs) in the presence of $Li_2CuCl_3$ or $Li_2CuCl_4$ was reported in *Tetrahedron* 1991, 47, 6287-6292 as shown below. However, this chemistry does not produce an olefinic product, but instead provides a potentially useful method for the preparation of long chain dichlorides which could themselves become candidates for conversion to long chain α,ω-olefins.

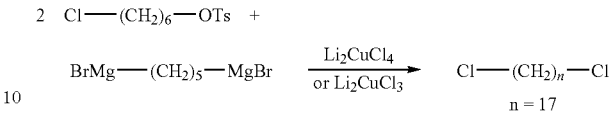

The present application describes a different and improved approach to the bulk synthesis of α,ω-olefins using this type of copper catalyzed coupling chemistry along with a significant improvement in the isolated yield over similar coupling reactions that use Grignard reagents.

The chemistry presented herein is of a type that does not require the use of extraordinary equipment (i.e. equipment that can handle higher pressure and temperature). However, the ability of the equipment to cryogenically cool the coupling reaction mixture is advantageous in order to maximize the yield and to improve the impurity profile (reduction of side reactions).

SUMMARY

The present application discloses an advantageous method for the industrial preparation of α,ω-olefins of the form $CH_2=CHCH_2(CH_2)_nCH_2CH=CH_2$ where n=3 to 24. In accordance with certain embodiments, the method provides an increase in yield and purity over other similar processes.

More particularly, a process for the synthesis of linear α,ω-diolefins from an allylic substrate is disclosed. In accordance with one aspect, the process comprises the steps of:
(a) forming the bis-Grignard reagent $XMgCH_2(CH_2)_n CH_2MgX$ from an α,ω-acyclic dihalide with X being a halogen;
(b) preparing a solution containing an allylic substrate and a copper catalyst;
(c) catalyzing a coupling reaction by adding to the solution of step (b) said bis-Grignard reagent of step (a); and
(d) isolating and purifying the α,ω-olefin coupling reaction product.

In accordance with certain aspects, the α,ω-diolefin may be an α,ω-symmetrical diene.

Typically reactions to form olefins of this type use allylmagnesium bromide coupled with a substrate which is a dihalide, ester (acetate) or a tosylate in the presence of catalytic lithium tetrachlorocuprate ($Li_2CuCl_4$) or lithium trichlorocuprate ($Li_2CuCl_3$). The present method couples an allyl halide (bromide or chloride), acetate or other allylic esters with a bis-Grignard reagent with the following formula:

$XMgCH_2(CH_2)_nCH_2M_gX$ where X=Br or Cl and n=1 to 18 that are obtained from the corresponding α,ω-acyclic dihalides. In accordance with particularly useful embodiments, the reactants are readily available. This method is superior to the literature method of reacting the less reactive dihalide, ester (acetate) or tosylate with allymagnesium halide as in *Synthetic Communications* 1994, 24, 459-463.

In accordance with certain aspects, the disclosed method increases the reactivity of the dihalide by converting it to the corresponding bis-Grignard and then coupling this active species with an allyl halide or allyl acetate which are already inherently reactive. The substrate for formation of the bis-Grignard reagent may also include straight chain dihalides. A particularly useful substrate is 2,6-dichloro-2,6-dimethyl-hexane which results in the formation of a particularly useful product, 4,4,7,7-tetramethyl-1,9-decadiene.

The bis-Grignard reagent formation can be carried out in an appropriate inert aprotic solvent system selected from among the group consisting of diethyl ether, diisopropyl ether, dibutyl ether, dimethoxyethane, dioxane, THF, cyclohexane, toluene, and mixtures thereof. THF is a particularly useful solvent.

The coupling reactions may be catalyzed with $Li_2CuCl_4$ or with $Li_2CuCl_3$. The concentration of catalyst typically is 0.1-10 mol % based on the amount of dihalide used to form the bis-Grignard reagent. Upon completion of the reaction the $\alpha,\omega$-olefin may be isolated in the usual way and then purified by distillation.

The present application also discloses a process where coupling is carried out by the sequence of adding the preformed (and if necessary pre-chilled) catalyst to either the allylic substrate or the Grignard reagent, and then adding the Grignard reagent to the chilled allylic substrate.

The present application also describes a process for obtaining dienes with improved yields comprising the process where a bis-Grignard when reacted with two moles of the allyl substrate, particularly an allyl halide, resulting in a higher yield in comparison to reacting two moles of allyl Grignard with the corresponding dihalides.

The disclosed process provides a practical process for synthesizing linear $\alpha,\omega$-diolefins such as 1,8-nonadiene, 1,9-decadiene, 1,10-undecadiene, 1,11-dodecadiene, 1,12-tridecadiene, 1,13-tetradecadiene, 1,14-pentadecadiene, 1,15-hexa-decadiene, 1,16-heptadecadiene, 1,17-octadecadiene, 1,18-nonadecadiene, 1,19-eicosadiene, and other long chain analogues.

The present method can also provide easy access to long chain symmetrical diolefins that are essential and valuable building blocks for various synthetic polymers and for the production of fine chemicals.

The use of 1,9-decadiene as a substrate has been described in over 100 U.S. patents or patent applications. The following are a few examples of potential applications: 1,9-decadiene is used in the production of a vinyl polymer having terminal functional groups as in U.S. Patent Application Publication No. 2008/0097049 as well as being part of an elastomeric composition for forming a golf ball or a component thereof as in U.S. Pat. No. 7,423,091. U.S. Patent Application Publication No. 2005/0031553 describes the use of an $\alpha,\omega$-symmetrical diene as a cross linker in the production of tooth whitening material. 1,9-Decadiene can also be used as a cross linker in controlled release drug delivery systems according to U.S. Pat. No. 6,048,522. Albemarle Corporation disclosed in U.S. Pat. No. 5,516,958 the use of 1,9-decadiene in a tri-n-octylaluminum catalyzed oligomerization reaction to exclusively form vinylidienes. The vinylidienes are used as lubricants and lubricant additives. 1,9-Decadiene is also used a cross linking agent in the formulation of a sunscreen as described in U.S. Pat. No. 5,145,669. The semi-conductor industry uses 1,9-decadiene as one of the preferred solvents in the manufacturing process due to the capability of the diene to scavenge ozone (see U.S. Patent Application Publication No. 2008/226941). The fine chemicals industry uses $\alpha,\omega$-symmetrical dienes for the production of monoene aldehydes and dialdehydes according to U.S. Pat. No. 7,145,042. In particular, 1,9-decadiene will produce 1,12-dodecanedial and/or undec-10-en-1-al using the BASF patented hydroformulation process (reactions are carried out using a rhodium catalyst in the presence of a ligand and about 145 psi of synthesis gas). The aldehyde group can be easily converted to many other functional groups such as the amino, hydroxyl and carboxy groups. The dialdehydes, diols, diamines and dicarboxylic acids thus obtained are suitable for many other applications. In an earlier patent a similar but higher pressure (claimed at the time to be low pressure) hydroformulation of dienes was reported by the Eastman Kodak Company (U.S. Pat. No. 4,742,178). Finally, according to U.S. Pat. No. 5,133,903 $\alpha,\omega$-symmetrical dienes will produce w-enecarboxylic acid esters which are valuable intermediates for the production of detergents, lubricants, emulsifiers, plasticizers, alkyd resins, polyamides, perfumes and flavors. The contents of the patent documents described above are incorporated herein by reference.

DETAILED DESCRIPTION

As was described above, one of the characteristic features of the methodology disclosed herein is the reaction of an allyl halide or allyl ester, more specifically allyl bromide, chloride, or acetate with a bis-Grignard reagent derived from an $\alpha,\omega$-dihalide. The dihalide may be a chloride, bromide, or iodide with the chloride being particularly useful due to decreased formation of the self (or Wurtz) coupling product. The dihalides may have a typical chain length of 3 to 10 carbons but are not restricted to those chain lengths. The only restriction is the use of a 2 carbon dihalide. Two examples of the coupling reaction are shown below.

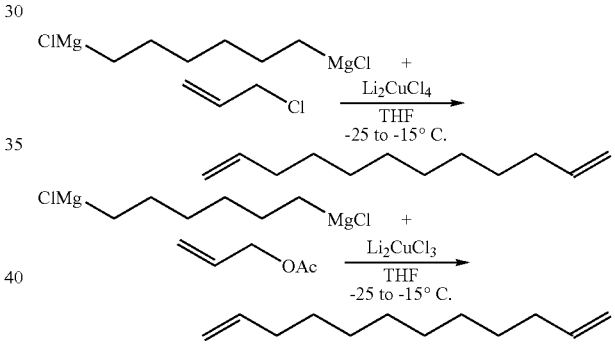

Grignard formation can be carried out in an ether or hydrocarbon solvent system comprising diethyl ether, diisopropyl ether, dibutyl ether, dimethoxyethane, dioxane, THF, cyclohexane, toluene, or mixtures thereof. Ether solvents are preferred over the hydrocarbon solvents with THF being a particularly useful solvent. The Grignard reagents are easily prepared by adding a THF solution of the dihalide over 30 minutes to 2 hours, preferably over 1 hour, to a suspension of magnesium metal (typically 2.05 to 2.30 equivalents) in the solvent of choice at a temperature between 25 and 70° C. In general the concentration of the resulting Grignard solution may be between 0.35 M and 0.80 M and may be about 0.5 M.

In a separate reactor the catalyst solution can be prepared by stirring 2 equivalents of LiCl with 1 equivalent of $CuCl_2$ to prepare $Li_2CuCl_4$ or with CuCl to prepare $Li_2CuCl_3$ in THF at 20 to 25° C. Typically the concentration of the catalyst solution is 0.09 M, but may be prepared as a more concentrated solution up to about 0.3 M. The amount of catalyst to prepare is based on the amount of the dihalide that is being used to form the Grignard reagent. The concentration of the catalyst may vary within wide limits. Typical catalyst loadings to be used in these coupling reactions may be as low as 0.1 mol % and as high as 10 mol %. Particularly preferred is a catalyst loading of 1-5 mol %.

The allyl halide, which can be generally in a 10 to 50 mol % excess may then be charged to the catalyst solution which is either at ambient temperature or has been pre-chilled to between −40° C. and 0° C. and preferably to between −35 and −25° C. Alternatively the allyl halide solution may be pre-chilled and the catalyst solution added. The Grignard solution which may be held at a temperature between 20 and 60° C. and preferably between 20 to 45° C. and more specifically between 20 to 30° C., may then be charged to the cold catalyst solution containing the allyl halide at a rate that will allow the desired reaction temperature range to be maintained. Addition times can range from 30 minutes up to a maximum of 3 hours with the preferable addition time being 1 to 2 hours. The reaction mixture may be stirred for between 30 minutes and 3 hours, with a 1 hour stir out being preferred, at about −10 to 10° C., and more specifically at 5° C. After the stir out is complete aqueous hydrochloric acid solution (generally 10% or 3 M) is then added to the cold reaction mixture. Alternatively water may be added followed by addition of concentrated hydrochloric acid to adjust the pH to between 2 and 7 and preferably to between 3 and 5. The organic layer may be diluted with a hydrocarbon solvent usually hexane or heptane to facilitate the layer break. Alternatively the ethereal solvent may be partially distilled from the reaction mixture prior to the aqueous workup and the addition of the hydrocarbon solvent. In some embodiments, this distilled solvent is then recycled into the next batch. The organic solution is washed with sodium chloride solution (5% solution up to saturated solution) or alternatively with ammonium chloride (5% solution up to saturated) and then with water or with saturated salt water. The product solution may be dried chemically ($MgSO_4$) or with azeotropic distillation of the solvent either at atmospheric pressure or under vacuum with the acceptable vacuum range being about 250 mm down to about 50 mm. Atmospheric distillation is preferable. The crude product may then be fractionally distilled under vacuum (typically 50 mm). The fractions are combined as appropriate to provide a purity that is not less than 97% and preferably ≧98.5%. Typical isolated distillation yields for this process are about 60%. It is also possible to use a wiped film (Luwa) distillation apparatus for purification of these compounds.

As an alternative method, it is potentially useful to chill the THF solution of the Grignard to the desired reaction temperature, charge the catalyst solution to the Grignard solution and then add the THF solution of the allyl halide over the desired time frame specified so as to maintain the desired reaction temperature (see description above). The workup, isolation procedure, and purification procedure are the same as above. Using this methodology does not appear to have a particularly deleterious effect on the outcome of the reaction and has the advantage in that the reaction becomes a one-pot synthesis; however, the reaction is more exothermic.

As was indicated above, the reaction temperature is typically between −40 and 0° C., preferably between −35 and −25° C. It should be noted that the reaction time does not necessarily decrease with increasing catalyst concentration although it could. This is due to the fact that all of the species that involved with the coupling reaction are inherently reactive. The catalyst is present so as to prevent undesirable side reactions and not necessarily to increase the rate of reaction (there is a contribution to the rate of reaction as well, although it is known that the species that are present will react with each other in the absence of the catalyst). Reaction time is extremely dependent upon the available cooling. As was noted above the coupling reaction is quite exothermic. A temperature differential of about 40° C. was observed during production runs. The reaction time is typically within the range of 30 minutes to 2 hrs and will be on the lower end of the scale with adequate cooling. The reactions are carried out discontinuously. A continuous process should not be disregarded since equipment is now available that would allow such a process to be successful. Grignard formation has been done in glass lined vessels up to 4000 gallons. This allows enough Grignard to be prepared to carry out several coupling reactions before more of the Grignard has to be prepared. The coupling reaction has been done in a 1000 gallon stainless vessel that has cryogenic capability. The suitable combination of the catalyst concentration, reaction temperature, and reaction time should be selected such that one who is skilled in the art can readily accomplish optimization with a few orienting experiments and interpolation or extrapolation.

Other features of the invention will become apparent in the course of the following description of exemplary embodiments which are given for illustration of the invention and are not intended to be limiting thereof.

Example 1

Synthesis of 1,9-Decadiene

Method A:

Magnesium turnings (63.35 g, 2.606 mol) were charged to a nitrogen purged reactor. THF was added to cover the turnings. 1,2-dibromoethane (10.88 g, 0.0579 mol) was added to activate the magnesium turnings. A solution of 1,4-dichlorobutane (147.08 g, 1.158 mol) in the remaining THF (total of 2300 mL) was prepared and added to the magnesium turnings at 60 to 66° C. The addition required 1.75 hours to complete. Note: the Grignard may also be initiated by adding 5 to 10% of the 1,4-dichlorobutane charge directly to the magnesium turnings and then warming the reaction mixture to 60 to 66° C. In a second reactor LiCl (1.963 g, 0.04632 mol) and $CuCl_2$ (3.114 g, 0.02316 mol) were combined in THF (260 mL). The mixture was stirred for 1 hour forming an orange solution. The catalyst solution was cooled to between −35 and −25° C. and allyl bromide (322.17 g, 2.663 mol) was charged to the catalyst solution. The Grignard solution was charged to the allyl bromide/catalyst solution over 55 minutes while holding the temperature within the desired range of −35 to −25° C. After the addition was complete, the reaction mixture was allowed to warm to 0 to 5° C. Stirring was continued for 1 h at that temperature. The reaction was quenched with 3 M aqueous hydrochloric acid solution (1000 mL). Hexane (200 mL) was added followed by stirring for a few minutes. The layers were separated. Aqueous saturated sodium chloride solution (500 mL) was added and the pH of the aqueous layer was adjusted to approximately 7 with aqueous potassium carbonate or with sodium bicarbonate. The sodium chloride wash was repeated one more time. The organic layer was dried ($MgSO_4$), filtered and concentrated at atmospheric pressure (64 to 80° C.) to yield 213.3 g of crude material that was 63.5% 1,9-decadiene which corresponds to an 84.6% yield.

Method B:

Magnesium turnings (19.66 g, 0.8087 mol) were charged to a nitrogen purged reactor. THF was added to cover the turnings. 1,2-dibromoethane (1.55 g, 0.0082 mol) was added to activate the magnesium turnings. A solution of 1,4-dichlorobutane (45.65 g, 0.3594 mol) in the remaining THF (total of 714 mL) was prepared and added to the magnesium turnings at 60 to 66° C. The addition required 2 hours to complete. In a second reactor LiCl (0.608 g, 0.0143 mol) and $CuCl_2$ (0.9665 g, 0.007189 mol) were combined in THF (81 mL). The mixture was stirred for 1 hour forming an orange solution after which the solution was cooled to about −25° C. The solution of Grignard reagent was transferred to the catalyst solution and the temperature was held at about −35° C. Allyl bromide (100.00 g, 0.8266 mol) was added over 50 minutes to the cold Grignard reagent/catalyst solution. The reaction mixture was warmed to about 0° C. over 30 minutes and held at that temperature for one hour. The reaction was quenched and the product isolated according to the procedure in Example 1.

Example 2

Synthesis of 1,11-Dodecadiene

Magnesium turnings (6.33 g, 260.53 mmol) were charged to a nitrogen purged reactor. THF was added to cover the turnings. 1,2-dibromoethane (1.09 g, 5.80 mmol) was added to activate the magnesium turnings. A solution of 1,6-dichlorohexane (18.33 g, 115.79 mmol) in the remaining THF (total of 230 mL) was prepared and added to the magnesium turnings at 45° C. The addition required one hour to complete, and the batch was at 65° C. In a second reactor LiCl (0.1963 g, 4.632 mmol) and CuCl (0.2293 g, 2.316 mmol) were combined in THF (26 mL). The mixture was stirred for 30 minutes forming an orange solution after which the solution was cooled to −25° C. Allyl acetate (26.67 g, 266.32 mmol) was added to the cold catalyst solution. The solution of Grignard reagent was transferred to the catalyst solution at a rated that would allow the temperature to be maintained between −25 and −15° C. The reaction mixture was warmed to about 0° C. over 20 minutes and held at that temperature for one hour. Analysis by GC or GC/MS indicated that the reaction was complete. The reaction was quenched and the product isolated according to the procedure in Example 1.

Typical $\alpha,\omega$-diolefins synthesized are 1,8-nonadiene, 1,9-decadiene, 1,10-undecadiene, 1,11-dodecadiene, 1,12-tridecadiene, 1,13-tetradecadiene, 1,14-pentadecadiene, 1,15-hexadecadiene, 1,16-heptadecadiene, 1,17-octadecadiene, 1,18-nonadecadiene, 1,19-eicosadiene, etc.; and derivatives of these which are substituted, other than on the double bonds, by alkyl, cycloalkyl, aryl, or aralkyl groups having 1-30 C atoms. Higher unsaturated hydrocarbons can be components of the chain, in addition to the above-named $\alpha,\omega$-diolefins.

Obviously, numerous modifications and variations of the present invention are possible in light of the above disclosure. It is therefore to be understood that within the scope of the appended claims, the invention may be practiced otherwise than as specifically described herein.

What is claimed is:

1. A process for the synthesis of linear $\alpha,\omega$-diolefins from an allylic substrate comprising the steps of:
   (a) forming a bis-Grignard reagent $XMgCH_2(CH_2)_n CH_2MgX$ wherein n=1 to 18 from an $\alpha,\omega$-acyclic dihalide with X being a halogen;
   (b) preparing a solution comprising an allylic substrate and a copper catalyst;
   (c) catalyzing a coupling reaction by adding to the solution of step (b) said bis-Grignard reagent of step (a); and
   (d) isolating and purifying the $\alpha,\omega$-olefin coupling reaction product.

2. The process of claim 1 wherein said $\alpha,\omega$-diolefin is an $\alpha,\omega$-symmetrical diene.

3. The process of claim 2 wherein said symmetrical diene contains from 5 to about 30 carbon atoms.

4. The process of claim 3 wherein said symmetrical diene is substituted other than at the terminal double bonds by alkyl, aryl, and cycloalkyl groups.

5. The process of according to claim 1 wherein said a, w acyclic dihalide contains a hydrocarbon chain length of from 3 to 10 carbons and the dihalide is a chloride or bromide.

6. The process of claim 1 wherein the said bis-Grignard reagent formation is carried out in an inert solvent system selected from the group consisting of diethyl ether, diisopropyl ether, dibutyl ether, dimethoxyethane, dioxane, tetrahydrofuran, cyclohexane, toluene, and mixtures thereof.

7. The process of claim 6 wherein the said solvent system comprises tetrahydrofuran.

8. The process of claim 1 wherein said allylic substrate is selected from the group consisting of allyl bromide, allyl chloride, allyl acetate, allyl propionate, isopropanoate, butyrate, iso-butyrate, sec-butyrate, t-butyl esters, allyl tosylate, and mixtures thereof.

9. The process of claim 1 wherein said catalyst is a lithium tetrachlorocuprate catalyst.

10. The process of claim 1 wherein said catalyst is a lithium trichlorocuprate.

11. The process of claim 1, wherein the concentration of said catalyst is 0.1-10 mol % based on the amount of dihalide used to form the bis-Grignard reagent.

12. The process of claim 1, wherein the reaction temperature is from about −40° C. to about 0° C.

13. The process of claim 1, wherein said coupling is carried out by combining the pre-formed catalyst with either the allylic substrate or the Grignard reagent, and then adding the Grignard reagent to the allylic substrate.

14. The process of claim 1 wherein said $\alpha,\omega$-diolefin is selected from the group consisting of 1,8-nonadiene, 1,9-decadiene, 1,10-undecadiene, 1,11-dodecadiene, 1,12-tridecadiene, 1,13-tetradecadiene, 1,14-pentadecadiene, 1,15-hexadecadiene, 1,16-heptadecadiene, 1,17-octa-decadiene, 1,18-nonadecadiene, and 1,19-eicosadiene.

* * * * *